United States Patent [19]

Harandi et al.

[11] Patent Number: 4,899,015
[45] Date of Patent: Feb. 6, 1990

[54] PROCESS FOR OLEFINS TO GASOLINE CONVERSION

[75] Inventors: Mohsen N. Harandi, Lawrenceville; Hartley Owen, Belle Mead, both of N.J.

[73] Assignee: Mobil Oil Corp., New York, N.Y.

[21] Appl. No.: 225,432

[22] Filed: Jul. 28, 1988

[51] Int. Cl.$^4$ .............................................. C07C 2/02
[52] U.S. Cl. ..................................... 585/533; 585/520
[58] Field of Search .............................. 585/520, 533

[56] References Cited

U.S. PATENT DOCUMENTS

| | | | |
|---|---|---|---|
| 4,456,781 | 6/1984 | Marsh et al. | 585/533 |
| 4,504,691 | 3/1985 | Hsia et al. | 585/533 |
| 4,554,396 | 11/1985 | Chang et al. | 585/533 |
| 4,746,762 | 5/1988 | Avidan et al. | 585/533 |

Primary Examiner—Curtis R. Davis
Attorney, Agent, or Firm—Alexander J. McKillop; Charles J. Speciale; L. Gene Wise

[57] ABSTRACT

An improved process is described for the conversion of olefins to gasoline in contact with zeolite type catalyst. Improvement comprises incorporating a fractionation step in the separation of the effluent stream from the olefins to gasoline conversion reactor such that LPG components in the effluent stream are separated and recovered as well as a stream comprising $C_5+$ gasoline range boiling liquids. In a preferred embodiment the fractionation step is integrated with FCC unsaturated gas plant fractionators providing advantages in the utilization of common fractionation equipment resulting in significant reduction in process energy and investment requirement.

9 Claims, 3 Drawing Sheets

PROCESS FOR OLEFINS TO GASOLINE CONVERSION

This invention relates to an improved process for the conversion of light olefins to gasoline boiling range hydrocarbons. In particular, the invention relates to an improved technique for the recovery and separation of liquified petroleum gas (LPG) from an olefins to gasoline conversion process effluent stream.

BACKGROUND OF THE INVENTION

Conversion of olefins to gasoline and/or distillate product is disclosed in U.S. Pat. Nos. 3,960,978 and 4,021,502 (Givens, Plank and Rosinski) wherein gaseous olefins in the range of ethylene to pentene, either alone or in admixture with paraffins, are converted into an olefinic gasoline blending stock by contacting the olefins with a catalyst bed made up of ZSM-5 or related zeolite. In U.S. Pat. Nos. 4,150,062 and 4,227,992 Garwood et al discloses the operating conditions for the Mobil Olefin to Gasoline/Distillate (MOGD) process for selective conversion of $C_3+$ olefins. A fluidized bed process for converting ethene-containing light olefinic streams, sometimes referred to as the Mobil Olefin to Gasoline (MOG) process is described by Avidan et al in U.S. Patent Application 006,407 filed 23 Jan 1987, now U.S. Pat. No. 4,746,762. The phenomena of shape-selective polymerization are discussed by Garwood in ACS Symposium Series No. 218, Intrazeolite Chemistry, "Conversion of $C_2-C_{10}$ to Higher Olefins over Synthetic Zeolite ZSM-5", 1983 American Chemical Society.

In the process for catalytic conversion of olefins to heavier hydrocarbons by catalytic oligomerization using an acid crystalline metallosilicate zeolite, such as ZSM-5 or related shape selective catalyst, process conditions can be varied to favor the formation of either gasoline or distillate range products. In the gasoline operating mode, or MOG reactor system, ethylene and the other lower olefins are catalytically oligomerized at elevated temperature and moderate pressure. Under these conditions ethylene conversion rate is greatly increased and lower olefin oligomerization is nearly complete to produce $C_5+$ hydrocarbons in good yield.

The olefins contained in an FCC gas plant are an advantageous feed for MOG. U.S. Pat. No. 4,090,949 discloses upgrading olefinic gasoline by conversion in the presence of carbon hydrogen-contributing fragments including olefins and a zeolite catalyst and where the contributing olefins may be obtained from a gas plant. U.S. Pat. Nos. 4,471,147 and 4,504,691 disclose an MOG/D process using an olefinic feedstock derived from FCC effluent. In these two latter patents the first step involves prefractionating the olefinic feedstock to obtain a gaseous stream rich in ethylene and a liquid stream containing $C_3+$ olefin.

The conventional MOG process design is concerned with converting ethylene in a fuel gas stream, such as an FCC off-gas, to gasoline. In the conventional MOG design no LPG recovery facility is provided since the LPG content of the MOG reactor effluent is relatively small. However, when it is desired to convert propene and/or butene to gasoline by processing olefinic-paraffinic LPG the unreacted paraffinic LPG, unconverted olefinic LPG and LPG produced in the conversion step constitute a significant portion of the MOG reactor effluent. In this case, processing the reactor effluent in the conventional MOG design is unacceptable since a major portion of reactor effluent LPG will be lost to fuel gas. However, with an adequate recovery and separation design for the LPG content of an MOG process converting $C_2-C_4$ olefins the performance of the MOG process could be improved where the process would represent a viable alternative to acid catalyzed alkylation as a route to high octane gasoline. Further, an economical recovery and separation step will open up the MOG process to utilize a wider range of available feedstock, particularly FCC light olefinic products, routinely available in the refinery setting. The provision of an improved MOG process as an alternative to the economically and environmentally beleaguered alkylation process would constitute a very noteworthy contribution to the options available to the refinery arts for the production of high octane.

Accordingly, it is an object of the present invention to provide an improved process for the conversion of light olefins, particularly $C_2-C_4$ olefins, to high octane gasoline.

Another object of the present invention is to present a useful design for the separation of LPG components from the reactor effluent and olefins to gasoline process.

Another object of the present invention is to provide the foregoing improved LPG recovery and separation process as an integral part of an FCC unsaturated gas plant and thereby confer improved economies upon the integrated process.

SUMMARY OF THE INVENTION

It has been discovered that the objectives of the present invention can be accomplished in a process wherein a fractionation step is incorporated into the recovery and separation of the effluent from the olefins to gasoline (MOG) process such that the LNG components of the effluent stream are separated and recovered as well as a stream comprising $C_5+$ gasoline range boiling liquids. In a preferred embodiment of the present invention the effluent stream is separated in high temperature and low temperature separators and the low boiling fraction is deethanized in a conventional absorber-sponge absorber system while higher boiling component, following stripping, is passed to the depropanizing-debutanizing section of the process.

It has further been discovered that the process of the present invention can be integrated with an unsaturated gas plant debutanizer upstream of the olefins to gasoline conversion reactor. In this embodiment the feedstream to the FCC debutanizer, comprising wild gasoline and FCC wet gas is passed to the FCC debutanizer and the vapor overhead fraction therefrom is passed to the MOG reactor system. Optionally the FCC debutanizer can be replaced with a depropanizer and a common debutanizer utilized to separate both the MOG effluent after deethanization and depropanization and the bottoms effluent from the FCC depropanizer.

More specifically, an improved process for the conversion for lower olefinic hydrocarbon feedstock to $C_5+$ gasoline range hydrocarbons has been discovered comprising: contacting a hydrocarbon stream containing $C_3-$ and/or $C_4-$ olefinic hydrocarbons with a medium pore shape selective solid catalyst in oligomerization zone under oligomerization conditions to produce an effluent stream rich in $C_5+$ gasoline range hydrocarbons; separating said effluent stream to provide a $C_3-$ hydrocarbon stream and a $C_3+$ hydrocarbon stream; fractionating said $C_3+$ hydrocarbon stream to produce a $C_5+$ gasoline range hydrocarbon stream, a stream rich in $C_4$ hydrocarbons and a stream rich in $C_3$ hydrocarbons.

DETAILED DESCRIPTION OF THE INVENTION

Figure 1:
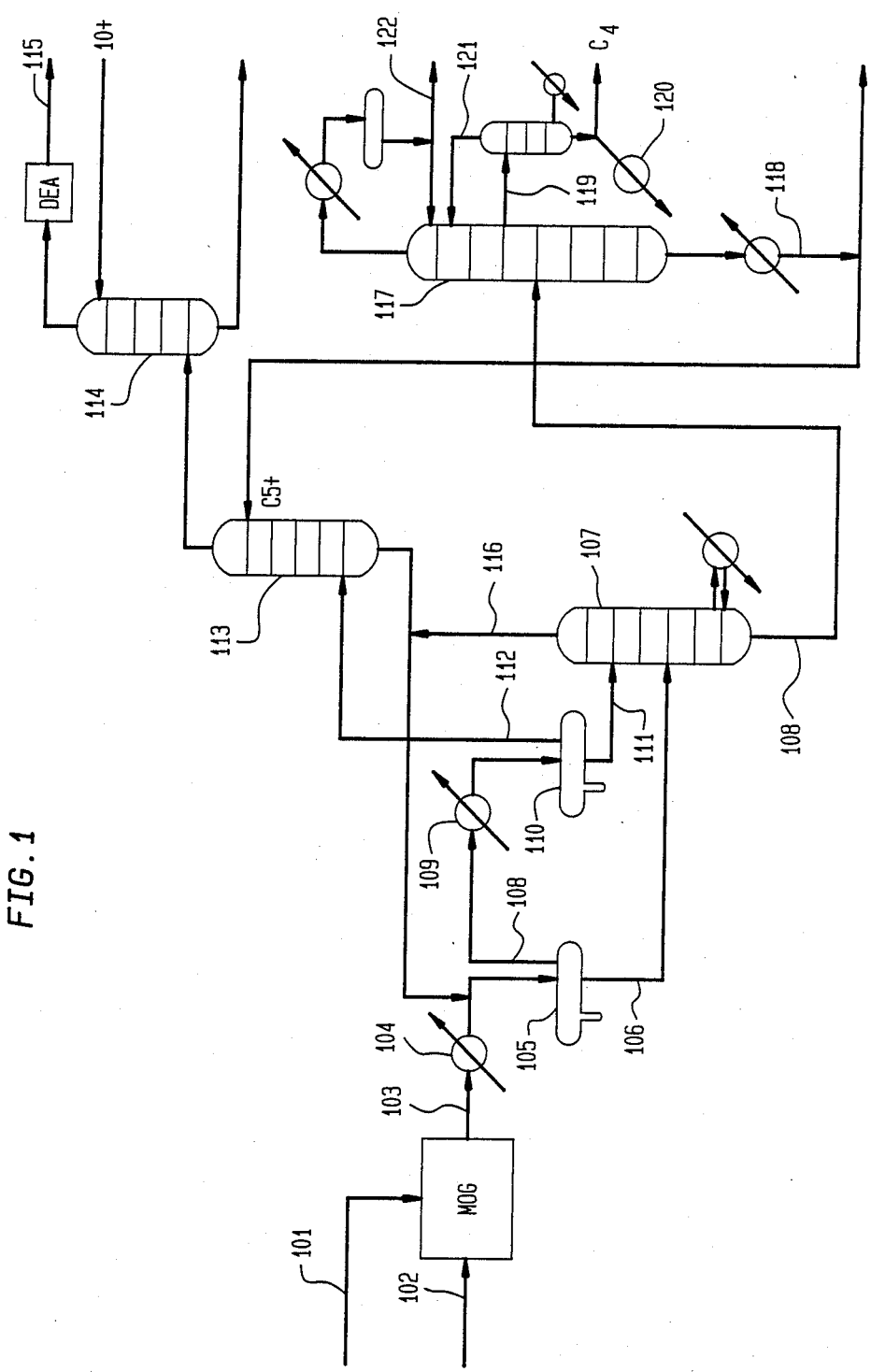
FIG. 1 is a schematic flow diagram illustrating the basic process design of the instant invention.

The present invention provides a system for upgrading light olefins such as FCC product components obtained from a FCC main column overhead product debutanizer or depropanizer, to liquid hydrocarbons. The invention utilizes a continuous process for producing fuel products by oligomerizing olefinic components to produce higher hydrocarbon products for use as fuel or the like. It provides a separation technique for use with processes for oligomerizing lower alkene-containing light gas feedstock, optionally containing ethene, propene, butenes or lower alkanes, to produce predominantly $C_5+$ hydrocarbons, including olefins.

The preferred feedstock contains $C_2-C_4$ alkenes (monoolefin) in the range of about 10 to 90 wt%. Non-deleterious components, such as methane and other paraffins and inert gases, may be present. A particularly useful feedstock is a light gas by-product of FCC gas oil cracking units containing typically 10–40 mol % $C_2-C_4$ olefins and 5–35 mol % $N_2$ with varying amounts of $C_1-C_3$ paraffins and inert gas, such as $N_2$. The process may be tolerant of a wide range of lower alkanes, from 0 to 95%. Preferred feedstocks contain more than 50 wt % $C_1-C_4$ lower aliphatic hydrocarbons, and contain sufficient olefins to provide total olefinic partial pressure of at least 50 kPa. Under the reaction severity conditions employed in the present invention lower alkanes, especially propane, may be partially converted to $C_4+$ products.

Conversion of lower olefins, especially ethene, propene and butenes, over HZSM-5 is effective at moderately elevated temperatures and pressures. The conversion products are sought as liquid fuels, especially the $C_5+$ hydrocarbons. Product distribution for liquid hydrocarbons can be varied by controlling process conditions, such as temperature, pressure and space velocity. Gasoline (eg, $C_5-C_9$) is readily formed at elevated temperature (e.g., up to about 400° C.) and moderate pressure from ambient to about 5500 kPa, preferably about 250 to 2900 kPa. Under appropriate conditions of catalyst activity, reaction temperature and space velocity, predominantly olefinic gasoline can be produced in good yield and may be recovered as a product. Operating details for typical olefin oligomerization units are disclosed in U.S. Pat. Nos. 4,456,779; 4,497,968 (Owen et al.) and 4,433,185 (Tabak), incorporated herein by reference. It has been found that $C_2-C_4$ rich olefinic light gas can be upgraded to liquid hydrocarbons rich in olefinic gasoline by catalytic conversion in a turbulent fluidized bed of solid acid zeolite catalyst under low severity reaction conditions in a single pass or with recycle of gaseous effluent components. This technique is particularly useful for upgrading LPG and FCC light gas, which usually contains significant amounts of ethene, propene, butenes, $C_2-C_4$ paraffins and hydrogen produced in cracking heavy petroleum oils or the like. It is a primary object of the present invention to provide a novel separation technique for use with upgrading such lower olefinic feedstock gasoline range hydrocarbons in an economic multistage reactor system.

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization catalyst preferred for use in olefins conversion includes the medium pore (i.e., about 5–7 angstroms) shape selective crystalline aluminosilicate zeolites having a silica to alumina ration of about 20:1 or greater, a constraint index of about 1-12, and acid cracking activity (alpha value) of about 10–200. Representative of the shape selective zeolites are ZSM-5, ZSM-11, ZSM-12, ZSM22, ZSM-23, ZSM-35, ZSM-38, and ZSM-48. ZSM-5 is disclosed in U.S. Pat. No. 3,702,886 and U.S. Pat. No. Reissue 29,948. Other suitable zeolites are disclosed in U.S. Pat. Nos. 3,709,979 (ZSM-11); 3,832,449 (ZSM-12); 4,076979; 4,076842 (ZSM-23); 4,016,245 (ZSM-35); and 4,375,573 (ZSM-48). The disclosures of these patents are incorporated herein by reference.

While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Bronsted acid sites may consist essentially of aluminosilicate ZSM-5 zeolite with 5 to 95 wt % silica, clay and/or alumina binder.

These siliceous zeolites may be employed in their acid forms ion exchanged or impregnated with one or more suitable metals, such as Ga, Pd, Zn, Ni, Co and/or other metals of Periodic Groups III to VIII. Ni-exchanged or impregnated catalyst is particularly useful in converting ethene under low severity conditions. The zeolite may include other components, generally one or more metals of group IV, IIB, IIIB, VA VIA or VIIIA of the Periodic Table (IUPAC). Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (eg, ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone. Certain of the ZSM-5 type medium pore shape selective catalysts are sometimes known as pentasils. In addition to the preferred aluminosilicates, the borosilicate, ferrosilicate and "silicalite" materials may be employed.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred.

A further useful catalyst is a medium pore shape selective crystalline aluminosilicate zeolite as described above containing at least one Group VIII metal, for example Ni-ZSM-5. This catalyst has been shown to convert ethylene at moderate temperatures and is disclosed in a copending U.S Patent Application Ser. No. 893,522, filed 4 Aug. 1986 by Garwood et al, now U.S. Pat. No. 4,717,782, incorporated herein be reference.

Referring now to FIG. 1, the novel process of the instant invention is shown which allows the utilization of LPG streams containing propene and butene as feedstock to the MOG process in addition to fuel gas containing ethene. Feedstock is introduced to the MOG reactor by conduits 101 and/or 102. In the present embodiment the feedstock may be drawn from any refinery source. The effluent from the conversion reactor is passed 103 after cooling 104 to a high temperature separator 105 for separation of a high boiling fraction 106 containing $C_5+$ hydrocarbons. That fraction is passed to stripper means 107. The vapor fraction 108 from the high temperature separator is cooled 109 and passed to a low temperature separator 110 and a higher boiling component of that fraction is separated and passed 111 to stripper 107. The light fraction 112 from separator 110 comprising light hydrocarbons is passed to absorber and sponge absorber system 113 and 114 for deethanization and recovery of $C_2-$ off-gas 115. The overhead fraction 116 from stripper 107 is recycled to the high temperature separator and the bottom fraction 108 comprising $C_4+$ hydrocarbons is passed through the novel depropanizer debutanizer of the present invention 117 where bottom $C_5+$ MOG gasoline fraction is separated 118. Stream 119 is withdrawn from a mid-portion of fractionator 117. This more efficiently separates $C_3$ and $C_4$ components as a bottom $C_4$ stream and an overhead $C_3$ stream 121 which is recycled to a top portion of fractionator 117 for separation as an overhead stream comprising $C_3$ hydrocarbons 122.

An important advantage of the present invention is to be found in those embodiments wherein the downstream separation of the effluent from an MOG reactor is integrated with an existing unsaturated gas plant such as the unsaturated gas plant (USGP) commonly incorporated as part of a fluid catalytic cracking (FCC) operation. The advantages inherent in these embodiments of the present invention lie in two general directions: the ability to double up on the utilization of USGP separation towers which affords a significant economic advantage in the costs associated with separation of the MOG reactor effluent; the opportunity to down-load USGP towers by shifting deethanization, depropanization and debutanization operations in large part to the towers integrated into the design of the MOG reactor effluent separation, inherent within the present invention.

Figure 2:
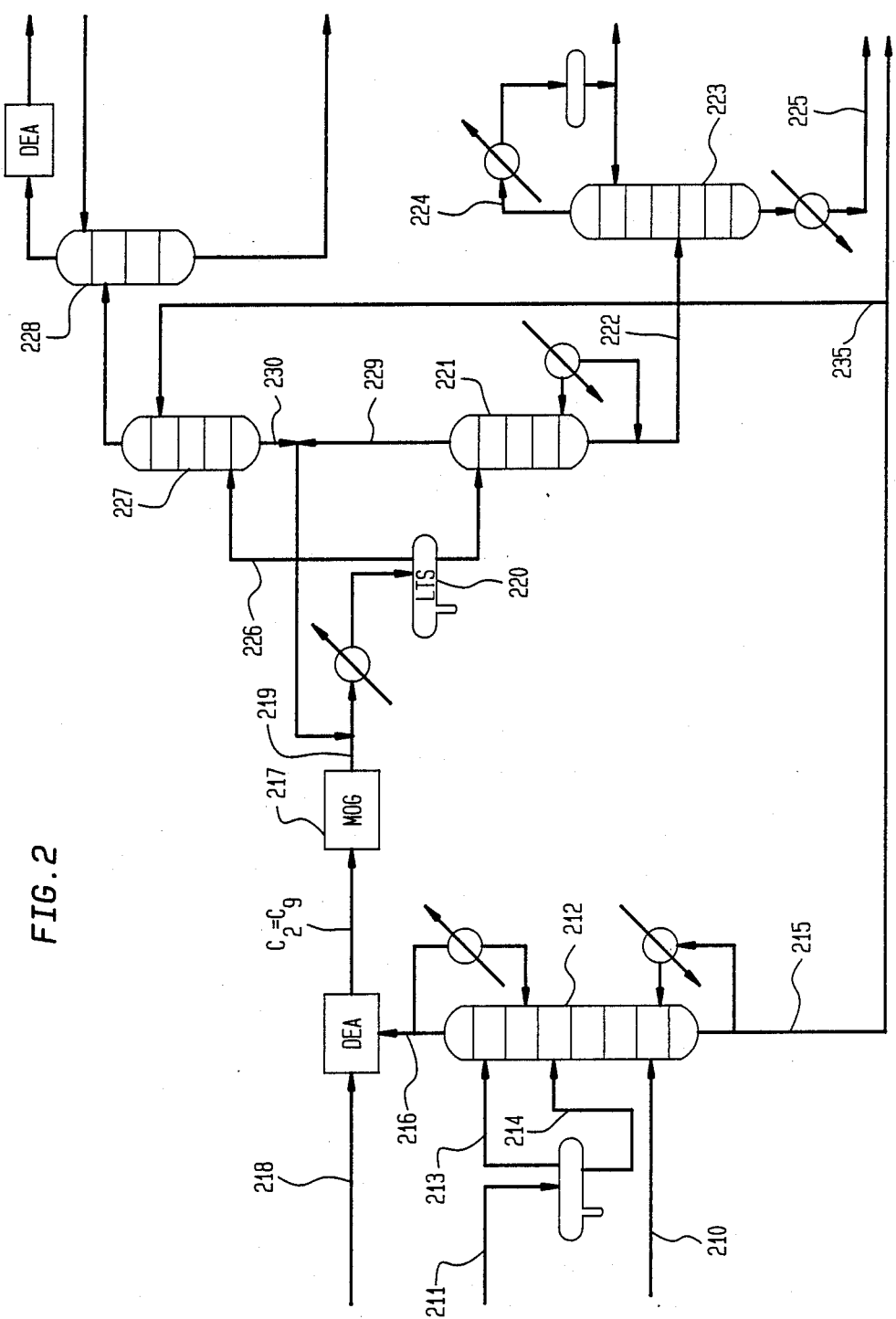
FIG. 2 is a flow diagram showing the novel MOG process integration with FCC unsaturated gas plant for the purpose of converting $C_4-$ olefins in MOG.
Figure 3:
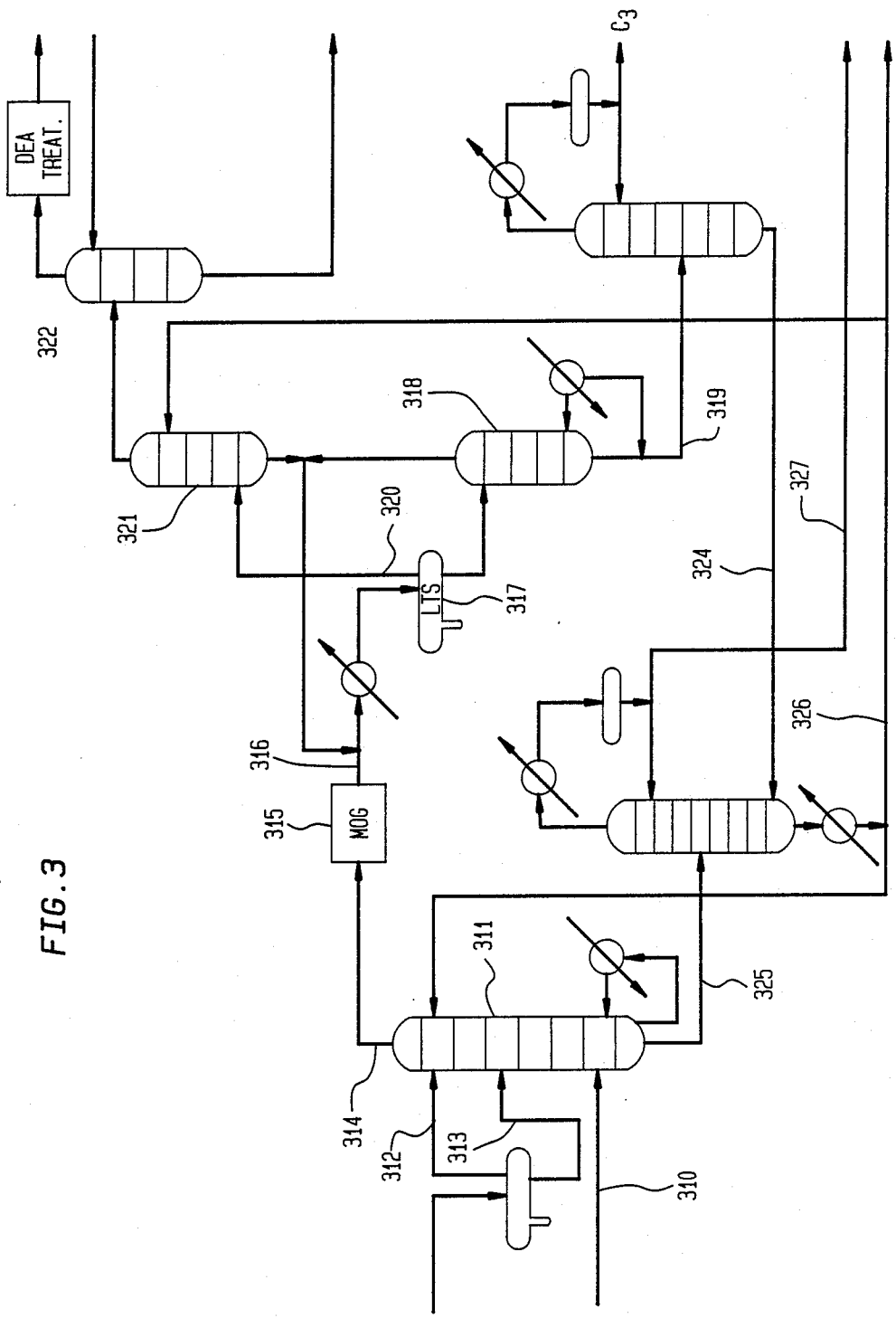
FIG. 3 is a process flow diagram further illustrating the novel MOG process integration with unsaturated gas plant for the purpose of converting $C_3-$ olefins in MOG.

FIGS. 2 and 3 present process flow diagrams representative of embodiments of the present invention wherein the invention involves an integration of the MOG product separation operations with unsaturated gas plant operations in a generic way, they are illustrative of the integration of MOG product effluent separation and USGP operation. The configuration of actual integrations may vary depending upon site specific and market specific opportunities in ways which can obviously be derived from the generic embodiments presented herein by those skilled in the art.

Referring now to FIG. 2, FCC wild gasoline 210 and the product outlet from the after-cooler from an FCC wet gas compressor 211 are passed to an FCC debutanizer 212 after separation of the after-cooler outlet stream into vapor and liquid components 213 and 214. A bottom stream 215 is separated from the debutanizer comprising $C_5+$ FCC gasoline and the overhead stream 216 comprising $C_4-$ hydrocarbons is passed to the MOG reactor 217. Optionally, feed from other process units comprising $C_2-C_4$ olefins is also passed 218 to the reactor. The MOG reactor effluent 219 is cooled and separated into liquid and vapor fractions in a low temperature separator 220. The liquid portion is passed to stripper 221 and the bottom portion therefrom is passed 222 to debutanizer 223 for separation into $C_4-$ overhead 224 and $C_5+$ MOG gasoline 225. Vapor from low temperature separator 220 is passed 226 to an absorber sponge absorber system 227, 228 for deethanization. A portion of stream 215 is passed 235 to absorber 227 as lean oil. The less volatile FCC gasoline stream 215 is the preferred lean oil because less volatile lean oil usage results in less gasoline carry over to the sponge absorber. The overhead from stripper 221 and the bottom fraction from absorber 227 is recycled 229 and 230 to low temperature separator 220.

FIG. 3 illustrates an embodiment of the present invention integrating MOG product separation with an FCC unsaturated gas plant utilizing a common debutanizer for separation of FCC and MOG product. Referring to FIG. 3, FCC wild gasoline is passed 310 to a depropanizer 311 in conjunction with the vapor and liquid fractions 312 and 313 from the FCC wet gas compressor after-cooler. $C_3-$ overhead is passed 314 as a feed stream to the MOG reactor 315. The effluent therefrom 316 is separated via low temperature separator 317 and stripper 318 to provide a $C_3+$ fraction 319 and an overhead fraction 320 which is deethanized in absorber system 321 and 322. In this case the bottom stripper fraction is passed to a depropanizer 323 and a $C_4+$ bottom fraction 324 is separated. This fraction is passed to a debutanizer in conjunction with the bottom fraction 325 from depropanizer 311. In the common debutanizer a bottom fraction is separated 326 comprising MOG and FCC $C_5+$ gasoline and an overhead fraction is collected 327 comprising MOG and FCC $C_4$ fractions.

In the following, (Table I) a comparison is presented showing the advantages of the present invention over conventional MOG operations. Column A shows the product distribution of an unsaturated gas plant, not incorporating an MOG process unit. Column B shows the product distribution of a conventional MOG operation which uses as a feedstock treated FCC sponge absorber stream. Column C shows a product distribution from MOG and USGP integration of the present invention represented by FIG. 2 process flow diagram. The results clearly show a distinctly superior yield of total gasoline product in the process of the instant invention.

TABLE I

MOG/USGP DESIGN EFFECT ON PRODUCT DISTRIBUTION

|  | Column A | Column B | Column C |
|---|---|---|---|
| MOG Gasoline(BPSD) | — | 780 | 5212 |
| FCC Gasoline (BPSD) | 30995 | 30995 | 30995 |
| Total Gasoline(BPSD) | 30995 | 31775 | 36207 |
| Butene(BPSD) | 4227 | 4163 | 273 |
| i-Butane (BPSD) | 1791 | 1840 | 2235 |
| n-Butane (BPSD) | 1134 | 1149 | 1150 |
| Total Liquid $C_4$'s | 7152 | 7152 | 3658 |
| Propene(BPSD) | 3775 | 3689 | 116 |
| Propane (BPSD) | 1155 | 1174 | 1191 |
| Total Liquid $C_3$'s | 4930 | 4863 | 1307 |
| Fuel Gas(MMSCFD) | 12.6 | 10.7 | 11.2 |

In Table II a comparison is presented of the equipment and energy fractionation requirements for an unsaturated gas plant alone and an integrated MOG/USGp unit. The comparison shows the advantages of MOG/USGP of the instant invention which can be operated with about the same energy usage and equipment requirements as a USGP along.

TABLE II

|  | Tower Diameter,Ft. | | Reboiler Duty (MMBTU/HR) | | Condenser Duty (MMBTU/HR) | |
|---|---|---|---|---|---|---|
|  | USGP | MOG/USGP | USGP | MOG/USGP | USGP | MOG/USGP |
| Sponge Absorber | 4.5 | 4.0 | 0 | 0 | 0 | 0 |
| Absorber/ Stripper | 8.5 | 6.0 | 70 | 27 | 0 | 0 |
| FCC Gasoline Debutanizer | 10.5 | 12.0 | 59 | 83 | 41 | 14 |
| MOG Gasoline Debutanizer | 0 | 6.0 | 0 | 27 | 0 | 18 |
| Depropanizer | 6.0 | 4.0 | 15 | 6 | 14 | 6 |

While the invention has been shown by describing preferred embodiments of the process, there is no intent to limit the inventive concept except as set forth in the following claims.

What is claimed is:

1. An improved process for the conversion of lower olefinic hydrocarbon feedstock to $C_5+$ gasoline range hydrocarbons comprising:
   a. contacting a hydrocarbon stream containing $C_3-$ and/or $C_4-$ olefinic hydrocarbons with a medium pore shape selective solid catalyst in an oligomerization zone under oligomerization conditions to produce an effluent stream rich in $C_5+$ gasoline range hydrocarbons;
   b. separating said effluent stream to provide a $C_3-$ hydrocarbon stream and a $C_3+$ hydrocarbon stream;
   c. fractionating said $C_3+$ hydrocarbon stream to produce a $C_5+$ gasoline range hydrocarbon stream, a stream rich in $C_4$ hydrocarbons and a stream rich in $C_3$ hydrocarbons.

2. The process of claim wherein step (b) separation of said effluent stream comprises passing said stream to high temperature and/or low temperature separators; passing the gaseous portion from said separators to absorber means whereby $C_2-$ hydrocarbon stream is produced and: passing liquid portion from said separators to a stripping means whereby $C_3+$ hydrocarbon stream is produced.

3. The process of claim 1 wherein step (c) fractionation of said $C_3+$ hydrocarbon stream comprises passing said stream to a depropanizer; separating an overhead stream rich in $C_3$ hydrocarbons, a bottom stream rich in $C_5+$ gasoline range liquid and a stream containing $C_4$ hydrocarbons; passing said $C_4$ hydrocarbon stream to a stripper for separation of a bottom stream therefrom rich in $C_4$ hydrocarbons and recycling said stripper overhead stream to said depropanizer.

4. The process of claim 1 wherein said lower olefinic hydrocarbon feedstock comprises the overhead effluent from FCC main column overhead product debutanizer or depropanizer.

5. The process of Claim 1 wherein step (c) fractionation comprises depropanizing to produce a $C_4+$ hydrocarbon stream; passing said stream to an FCC debutanizer for separation; recovering a bottom stream comprising $C_5+$ gasoline range hydrocarbon and an overhead stream comprising $C_4$ hydrocarbons.

6. The process of claim wherein said solid catalyst comprises zeolite type metallosilicate.

7. The process of claim 6 wherein said zeolite type metallosilicate comprises ZSM-5.

8. The process of claim 4 wherein bottoms fraction of said FCC depropanizer is passed to debutanizer in combination with $C_4+$ fraction from said oligomerization zone.

9. A process for oligomerizing lower olefins to produce gasoline range liquid hydrocarbons comprising: contacting an ethene rich hydrocarbon stream with acid metallosilicate solid catalyst in an oligomerization zone under oligomerization conditions; separating oligomerization reaction effluent in a low temperature separator; passing a vapor stream from the separator to an absorber for contact with liquid hydrocarbons to recover $C_{231}-$hydrocarbons; recovering a liquid stream from the low temperature separator comprising volatile $C_3+$gasoline; stripping the low temperature separator liquid stream to recover a bottom stripping fraction comprising $C_3+$hydrocarbons; passing said bottom stripping fraction to a fractionator for separation of an overhead stream comprising $C_3$ hydrocarbons, a bottom stream comprising $C_5+$gasoline liquids and a stream comprising $C_4$ hydrocarbons.

* * * * *

UNITED STATES PATENT AND TRADEMARK OFFICE
CERTIFICATE OF CORRECTION

PATENT NO. : 4,899,015

DATED : February 6, 1990

INVENTOR(S) : Harandi and Owen

It is certified that error appears in the above-identified patent and that said Letters Patent is hereby corrected as shown below:

Column 7, line 59, add "1" after "claim"

Column 8, line 23, add "1" after "claim"

Column 8, line 54, change "$C_{231}$" to "$C_2$"

Signed and Sealed this

Twenty-second Day of October, 1991

Attest:

HARRY F. MANBECK, JR.

Attesting Officer

Commissioner of Patents and Trademarks